United States Patent [19]

Stanek et al.

[11] Patent Number: 4,968,804

[45] Date of Patent: Nov. 6, 1990

[54] BIPYRIDINE COMPOUNDS

[75] Inventors: Jaroslav Stanek, Arlesheim; Giorgio Caravatti, Allschwil; Jörg Frei, Hölstein; Hans-Georg Capraro, Rheinfelden, all of Switzerland

[73] Assignee: Ciba-Geigy Corporation, Ardsley, N.Y.

[21] Appl. No.: 375,760

[22] Filed: Jul. 5, 1989

[30] Foreign Application Priority Data

Jul. 7, 1988 [CH]  Switzerland .................. 2588/88

[51] Int. Cl.⁵ .................. A61K 31/44; C07D 401/04
[52] U.S. Cl. .................................................. 546/257
[58] Field of Search ........................................ 546/257

[56] References Cited

U.S. PATENT DOCUMENTS

| | | | |
|---|---|---|---|
| 4,086,244 | 4/1978 | Sprague | 260/340.3 |
| 4,233,968 | 11/1980 | Shaw, Jr. | 128/130 |
| 4,284,074 | 8/1981 | Shaw, Jr. | 128/130 |
| 4,359,046 | 11/1982 | Shaw, Jr. | 128/130 |
| 4,381,001 | 4/1983 | Shaw, Jr. | 128/130 |
| 4,493,726 | 1/1985 | Burdeska et al. | 71/87 |
| 4,495,934 | 1/1985 | Shaw, Jr. | 128/130 |
| 4,598,073 | 7/1986 | Newkome | 514/185 |
| 4,674,229 | 6/1987 | Burdeska et al. | 47/57.6 |

FOREIGN PATENT DOCUMENTS

| | | |
|---|---|---|
| 024779 | 3/1981 | European Pat. Off. . |
| 024780 | 3/1981 | European Pat. Off. . |
| 024781 | 3/1981 | European Pat. Off. . |
| 55693 | 7/1982 | European Pat. Off. . |

OTHER PUBLICATIONS

J. Am. Chem. Soc, vol. 80, pp. 2745–2748 (1958) Maerker.
J. Am. Chem. Soc., vol. 104, pp. 7519–7526 (1982) Elliott.
Chemical Abstracts, vol. 105, No. 72085r (1986).
Chem. Abstracts, vol. 105, No. 90903k (1986).
Chem. Abstracts, vol. 109, No. 242947a (1988).
Chem. Abstracts, vol. 88, No. 37578n (1978).
Antonini et al., J. Med. Chem. vol. 24 pp. 1181–1184 (1981).
Chem. Abstr. 52: 18415e (1958).
Chem. Abstr. 53: 11087d (1959).
Chem. Abstr. 58: 12460d (1963).
Chem. Abstr. 98: 97743d (1983).

Primary Examiner—Alan L. Rotman
Assistant Examiner—Joseph K. McKane
Attorney, Agent, or Firm—Irving M. Fishman

[57] ABSTRACT

Compounds of formula I

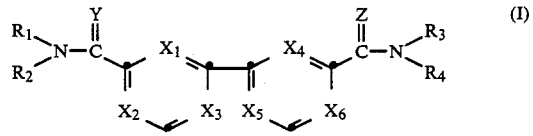

wherein $X_1$, $X_2$, $X_3$, $X_4$, $X_5$, $X_6$, Y, Z and $R_1$–$R_4$ are as defined in the description, have valuable pharmaceutical properties and are especially active against tumours. They are prepared in a manner known per se.

13 Claims, No Drawings

BIPYRIDINE COMPOUNDS

The invention relates to compounds of formula I

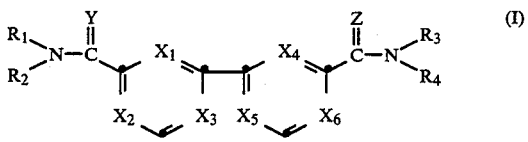

wherein each of $X_1$, $X_2$ and $X_3$, independently of the others, is CH or N, with proviso that at least one of the groups $X_1$, $X_2$ and $X_3$ is CH; each of $X_4$, $X_5$ and $X_6$, independently of the others, is CH or N, with the proviso that at least one of the groups $X_4$, $X_5$ and $X_6$ is CH; Y is $NR_5$, O or S, Z is $NR_6$, O or S, each of the radicals $R_2$, $R_4$, $R_5$ and $R_6$, independently of the others, is hydrogen or lower alkyl and each of the radicals $R_1$ and $R_3$, independently of the other, is hydrogen, lower alkyl, cycloalkyl, aryl-lower alkyl, aryl, free or functionally modified carboxy, hydroxy, etherified or esterified hydroxy or unsubstituted or mono- or di-substituted amino; wherein the radicals $R_1$ and $R_2$ together may also be lower alkylene, wherein the radicals $R_3$ and $R_4$ together may also be lower alkylene, wherein the radicals $R_2$ and $R_5$ together may also be lower alkylene, and wherein the radicals $R_4$ and $R_6$ together may also be lower alkylene; with the proviso that Y is $NR_5$ or S and Z is $NR_6$ or S when $X_3$ and $X_5$ are N and $X_1$, $X_2$, $X_4$ and $X_6$ are CH; and with the proviso that Y is $NR_5$ and Z is $NR_6$ when (a) $X_4$ and $X_5$ are N and $X_1$, $X_2$, $X_3$ and $X_6$ are CH or (b) $X_1$ and $X_3$ are N and $X_2$, $X_4$, $X_5$ and $X_6$ are CH; tautomers thereof, and salts thereof, processes for the preparation of those compounds, pharmaceutical preparations containing those compounds, the use of those compounds for the therapeutic treatment of the human or animal body or for the manufacture of pharmaceutical preparations. Tautomers may occur, for example, when Y is $NR_5$ and $R_1$ and/or $R_2$ are/is hydrogen:

The corresponding amidine radical, shown in formula I as $-C(=Y)-NR_1R_2$, may then, for example, also be in the tautomeric forms $-C(-YH)=NR_1$ or $-C(-YH)=NR_2$.

A further example: When Z is $NR_6$ and $R_3$ and/or $R_4$ are/is hydrogen, then the corresponding amidine structure, shown in formula I as $-C(=Z)-NR_3R_4$, may also be in the tautomeric forms $-C(-ZH)=NR_3$ or $-C(-ZH)=NR_4$. The person skilled in the art is familiar with the occurrence of these and similar tautomers. All these tautomers are covered by the general formula I.

Within the scope of the present Application, the general terms used hereinbefore and hereinafter preferably have the following meanings:

The prefix "lower" denotes a radical having from 1 to 7 and especially from 1 to 4 carbon atoms.

Lower alkyl is, for example, n-propyl, isopropyl, n-butyl, isobutyl, sec.-butyl, tert.-butyl, n-pentyl, neopentyl, n-hexyl or n-heptyl, preferably ethyl and especially methyl.

Cycloalkyl contains, for example, from 3 to 8, preferably 5 or 6, ring carbon atoms and is, for example, cyclopropyl, cyclopentyl, cyclohexyl or cycloheptyl.

Aryl-lower alkyl is preferably phenyl-lower alkyl and especially benzyl.

Aryl is, for example, phenyl or naphthyl, such as 1- or 2-naphthyl. The phenyl or naphthyl radicals may be unsubstituted or substituted. Aryl is preferably phenyl that is unsubstituted or substituted by lower alkyl, lower alkoxy, halogen and/or by nitro, and is especially phenyl.

Free or functionally modified carboxy is preferably cyano, and also, for example, carboxy, esterified carboxy, such as, for example, lower alkoxycarbonyl, or amidated carboxy, such as, for example, carbamoyl ($-CONH_2$), N-lower alkylcarbamoyl or N,N-di-lower alkylcarbamoyl.

Etherified hydroxy is, for example, lower alkoxy. Esterified hydroxy is, for example, lower alkanoyloxy. Mono-substituted amino is, for example, lower alkylamino. Di-substituted amino is, for example, di-lower alkylamino, $C_4$–$C_6$alkyleneamino, for example piperidino, oxa-$C_3$–$C_5$alkyleneamino, for example morpholino, thia-$C_3$–$C_5$alkyleneamino, for example thiomorpholino, or aza-$C_3$–$C_5$alkyleneamino that is unsubstituted or substituted by lower alkyl at the aza nitrogen atom, for example piperazino or 4-lower alkylpiperazino. Di-substituted amino is preferably di-lower alkylamino.

Lower alkylene formed by the groups $R_1$ and $R_2$ or $R_3$ and $R_4$ is preferably $C_2$–$C_7$alkylene and especially $C_4$–$C_5$alkylene, for example 1,4-butylene or 1,5-pentylene.

Lower alkylene formed by the groups $R_2$ and $R_5$ or $R_4$ and $R_6$ is preferably $C_2$–$C_5$alkylene and especially $C_2$–$C_3$alkylene, for example 1,2-ethylene or 1,3-propylene.

Halogen is, for example, fluorine or iodine, especially bromine and more especially chlorine.

Salts of compounds according to the invention are especially pharmaceutically acceptable non-toxic salts. For example, compounds of formula I having basic groups can form acid addition salts, for example with inorganic acids, such as hydrochloric acid, sulfuric acid or phosphoric acid, or with suitable organic carboxylic or sulfonic acids, for example acetic acid, fumaric acid or methanesulfonic acid, or, for example, with amino acids, such as arginine or lysine. When several basic groups are present, mono- or poly-salts may be formed. Compounds of formula I having an acid group, for example carboxy, and a basic group, for example amino, may be, for example, in the form of internal salts, that is to say in zwitterionic form, or one part of the molecule may be in the form of an internal salt and another part may be in the form of a normal salt.

For isolation or purification, it is also possible to use pharmaceutically unsuitable salts, for example picrates or perchlorates. Only the pharmaceutically acceptable non-toxic salts are used therapeutically and those are therefore preferred.

Depending on their chemical structure, the compounds of the present invention may be in the form of mixtures of isomers or in the form of pure isomers.

The compounds according to the invention have valuable, especially pharmacologically acceptable, properties. They have, especially, a strong, specific inhibiting effect on the enzyme S-adenosylmethionine decarboxylase (SAMDC). SAMDC, as a key enzyme, plays an important part in polyamine synthesis which occurs in practically all the cells of mammals, including humans. SAMDC regulates the polyamine concentration in the cell. Inhibition of the enzyme SAMDC results in a reduction in the polyamine concentration.

Since a reduction in the polyamine concentration causes inhibition of cell growth, it is possible, by administering SAMDC-inhibiting substances, to inhibit the growth of both eukaryotic and prokaryotic cells and even to kill cells or inhibit the commencement of cell differentiation.

Inhibition of the enzyme SAMDC can be demonstrated, for example, using the method of H. G. Williams-Ashmann and A. Schenone, Biochem. Biophys. Res. Communs. 46. 288 (1972). Illustrative compounds of the invention have IC$_{50}$ values of approximately 1 $\mu$M.

An advantage of the compounds according to the invention is that they inhibit diaminoxidase only to a small extent in comparison with their strong inhibiting action on SAMDC and are well tolerated. According to J. Jaenne and D. R. Morris, Biochem. J. 218, 974 (1984), the inhibition of diaminoxidase is disadvantageous since it can lead to the accumulation of putrescine and an indirect activation of SAMDC.

The compounds of formula I can therefore be used, for example, for the treatment of benign and malignant tumours. They are able to bring about tumour regression and also to prevent the spread of tumour cells and the growth of micrometastases. Furthermore, they can be used, for example, for the treatment of protozoa infections, such as, for example, trypanosomiasis, malaria or inflammation of the lungs caused by *Pneumocystis carinii*.

As selective SAMDC-inhibitors, the compounds of formula I can be used on their own or in combination with other pharmacologically active substances. Possible combinations are, for example, those with (a) inhibitors of other enzymes of polyamine biosynthesis, for example ornithine decarboxylase inhibitors, (b) inhibitors of protein kinase C, (c) inhibitors of tyrosine protein kinase, (d) cytokines, (e) negative growth-regulators, (f) aromatase inhibitors, (g) anti-oestrogens or (h) classical cytostatically active substances.

Preferred are the compounds of formula I wherein each of $X_1$, $X_2$ and $X_3$, independently of the others, is CH or N, with the proviso that at least one of the groups $X_1$, $X_2$ and $X_3$ is CH; each of $X_4$, $X_5$ and $X_6$, independently of the others, is CH or N, with the proviso that at least one of the groups $X_4$, $X_5$ and $X_6$ is CH; Y is NH, O or S, Z is NH, O or S, each of the radicals $R_2$ and $R_4$, independently of the other, is hydrogen or lower alkyl and each of the radicals $R_1$ and $R_3$, independently of the other, is hydrogen, lower alkyl, $C_3$-$C_8$cycloalkyl, phenyl-lower alkyl, phenyl, carboxy, hydroxy or amino; wherein the radicals $R_1$ and $R_2$ together may also be $C_2$-$C_7$alkylene, and wherein the radicals $R_3$ and $R_4$ together may also be $C_2$-$C_7$alkylene; with the proviso that Y and Z are NH or S when $X_3$ and $X_5$ are N and $X_1$, $X_2$, $X_4$ and $X_6$ are CH; and with the proviso that Y and Z are NH when (a) $X_4$ and $X_5$ are N and $X_1$, $X_2$, $X_3$ and $X_6$ are CH, or (b) $X_1$ and $X_3$ are N and $X_2$, $X_4$, $X_5$ and $X_6$ are CH; tautomers thereof, and salts thereof.

Especially preferred are the compounds of formula I wherein each of $X_1$, $X_2$ and $X_3$, independently of the others, is CH or N, with the proviso that at least one of the groups $X_1$, $X_2$ and $X_3$ is CH; each of $X_4$, $X_5$ and $X_6$, independently of the others, is CH or N, with the proviso that at least one of the groups $X_4$, $X_5$ and $X_6$ is CH; Y is NH, Z is NH, each of the radicals $R_2$ and $R_4$, independently of the other, is hydrogen or lower alkyl and each of the radicals $R_1$ and $R_3$, independently of the other, is hydrogen, lower alkyl, $C_3$-$C_8$cycloalkyl, phenyl-lower alkyl, phenyl, carboxy, hydroxy or amino; wherein the radicals $R_1$ and $R_2$ together may also be $C_2$-$C_7$alkylene, and wherein the radicals $R_3$ and $R_4$ together may also be $C_2$-$C_7$alkylene; tautomers thereof, and salts thereof.

Very especially preferred are the compounds of formula I wherein (a) $X_1$ and $X_4$ are N and $X_2$, $X_3$, $X_5$ and $X_6$ are CH or (b) $X_2$ and $X_6$ are N and $X_1$, $X_3$, $X_4$ and $X_5$ are CH; Y is NH or O, Z is NH or O, the radicals $R_2$ and $R_4$ are hydrogen and the radicals $R_1$ and $R_3$ are hydrogen, lower alkyl, hydroxy or amino, tautomers thereof, and pharmaceutically acceptable salts thereof.

More especially preferred are the compounds of formula I wherein (a) $X_1$ and $X_4$ are N and $X_2$, $X_3$, $X_5$ and $X_6$ are CH or (b) $X_2$ and $X_6$ are N and $X_1$, $X_3$, $X_4$ and $X_5$ are CH; Y is NH, Z is NH, the radicals $R_2$ and $R_4$ are hydrogen and the radicals $R_1$ and $R_3$ are hydrogen, lower alkyl, $C_5$-$C_6$-cycloalkyl or hydroxy, tautomers thereof, and pharmaceutically acceptable salts thereof.

As sub-groups of a group of compounds of formula I, prominence is to be given to each of the following: (a) compounds of formula I wherein the groups —C(=Y)—NR$_1$R$_2$ and —C(=Z)—NR$_3$R$_4$ are identical; (b) compounds of formula I wherein the groups

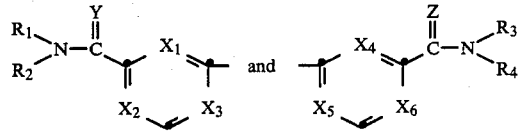

are identical; (c) compounds of formula I wherein the symbols $X_1$-$X_6$ have the following meanings:
(1) $X_1$=$X_4$=N and $X_2$=$X_3$=$X_5$=$X_6$=CH or
(2) $X_2$=$X_6$=N and $X_1$=$X_3$=$X_4$=$X_5$=CH or
(3) $X_3$=$X_5$=N and $X_1$=$X_2$=$X_4$=$X_6$=CH or
(4) $X_1$=$X_2$=$X_3$=$X_4$=$X_5$=$X_6$=CH or
(5) $X_4$=N and $X_1$=$X_2$=$X_3$=$X_5$=$X_6$=CH or
(6) $X_5$=N and $X_1$=$X_2$=$X_3$=$X_4$=$X_6$=CH or
(7) $X_6$=N and $X_1$=$X_2$=$X_3$=$X_4$=$X_5$=CH or
(8) $X_5$=$X_6$=N and $X_1$=$X_2$=$X_3$=$X_4$=CH or
(9) $X_4$=$X_6$=N and $X_1$=$X_2$=$X_3$=$X_5$=CH;
(d) compounds of formula I wherein the symbols $X_1$-$X_6$ have the meanings (1), (2), (3) or (4) given under (c); (e) compounds of formula I wherein $R_1$, $R_2$, $R_3$ and $R_4$ are hydrogen; (f) compounds of formula I wherein at least one of the groups $X_1$-$X_6$ is N.

The invention relates most especially to the specific compounds described in the Examples and to pharmaceutically acceptable salts thereof.

The compounds of formula I can be prepared in a manner known per se by, for example, in a compound of formula II

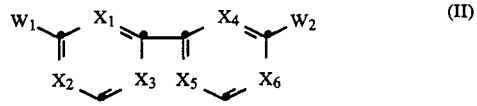

wherein each of $W_1$ and $W_2$ is a radical that can be converted into the groups —C(=Y)NR$_1$R$_2$ and —C(=Z)NR$_3$R$_4$, respectively, converting the radicals $W_1$ and $W_2$ into the groups —C(=Y)NR$_1$R$_2$ and —C(=Z)NR$_3$R$_4$, respectively; wherein the symbols $X_1$-$X_6$, Y, Z and $R_1$-$R_4$ are as defined under formula I; and/or converting a resulting compound of formula I into a different compound of formula I, and/or converting a resulting salt into the free compound or into a different salt, and/or converting a resulting free compound of formula I having salt-forming properties into a salt.

In the following more detailed description of the process, each of the symbols $X_1-X_6$, Y, Z and $R_1-R_6$ is as defined under formula I, unless otherwise indicated.

In the intermediates of formula II, $W_1$ and $W_2$ are, for example, free or functionally modified carboxy, especially halocarbonyl, carbamoyl, N-lower alkylcarbamoyl, cyano, an imino-lower alkyl ester [—C(=N-H)—OAlk (Alk   lower alkyl)]

or imino-lower alkylthiol ester [—C(=NH)—SAlk].

In the preparation of (mono- or di-)amidines of formula I (Y   NR$_5$ and/or Z   NR$_6$)

the groups $W_1$ and/or $W_2$ in a compound of formula II may be, for example: an acid addition salt of an imino-lower alkyl ester ( imino-lower alkyl ether)

or imino-lower alkylthiol ester, for example —C(=N-H)—OC$_2$H$_5$ · HCl or —C(=NH)—SC$_2$H$_5$ · HI, respectively, cyano or N-lower alkylcarbamoyl.

Reaction of (mono- or di-)imino-lower alkyl esters or (mono- or di-)-imino-lower alkylthiol esters of formula II (in the form of salts) with ammonia or with primary or secondary amines yields the unsubstituted or mono- or di-substituted (mono- or di-)amidines of formula I, respectively. (Mono- or di-)cyano compounds of formula II can be converted into an unsubstituted or mono- or di-substituted (mono- or di-)amidine of formula I, for example, by reaction with an alkali metal amide, for example KNH$_2$, or by reaction with a primary or secondary (di-)lower alkylammonium halide, for example N$^\ominus$H$_3$CH$_3$ Cl$^\oplus$.

Compounds of formula II wherein $W_1$ and/or $W_2$ are/is N-lower alkylcarbamoyl can be converted, for example by reaction with POCl$_3$ or PCl$_5$, into the corresponding imidic acid chlorides [—C(=NH-Alk)—Cl] which, after reaction with ammonia or with a primary or secondary amine, yield substituted (mono- or di-)amidines of formula I [see Chem. Abstr. 81, 91185a (1974)].

Compounds of formula I wherein the radicals R$_2$ and R$_5$ together and/or the radicals R$_4$ and R$_5$ together are lower alkylene can be prepared, for example, by reacting a compound of formula II wherein $W_1$ and/or $W_2$ are/is cyano with an α,ω-diamino-lower alkane, for example 1,2-diaminoethane, preferably in the presence of catalytic amounts of carbon disulfide.

In the preparation of (mono- or di-)carbamoyl compounds of formula I (Y   O and/or Z   O)

the groups $W_1$ and/or $W_2$ in a compound of formula II may be, for example: carboxy, halocarbonyl (for example —COCl). lower alkoxycarbonyl or cyano. The formation of unsubstituted or mono- or di-substituted (mono- or di-)carbamoyl compounds of formula I from corresponding intermediates of formula II wherein $W_1$ and/or $W_2$ are/is carboxy, halocarbonyl or lower alkoxycarbonyl by reaction with ammonia or with primary or secondary amines is known per se. Intermediates of formula II wherein $W_1$ and/or $W_2$ are/is cyano can be converted into unsubstituted or mono- or di-substituted (mono- or di-)carbamoyl compounds of formula I, for example by partial hydrolysis, in the manner of a Graf-Ritter reaction, or by way of imino-lower alkyl ester salts. The conditions in the hydrolysis of the cyano intermediates may be so chosen that the reaction is broken off at the amide stage. Hydrolysis with acids is especially suitable for that purpose, there coming into consideration, for example, 80% sulfuric acid (with heating), polyphosphoric acid (at 100°-150° C.), hydrogen bromide/glacial acetic acid (room temperature, formic acid or without solvent), HCl gas in ethereal solution followed by the addition of water or aqueous hydrochloric acid, or boron halides.

Using the Graf-Ritter reaction, it is also possible to prepare N-substituted amides from (mono- or di-)nitriles of formula II. For that purpose, the (mono- or di-)nitriles are reacted in the presence of a strong acid, especially 85-90% sulfuric acid, or alternatively polyphosphoric acid, formic acid, boron trifluoride or other Lewis acids, but not aluminium chloride, with compounds that are capable of forming carbenium ions in the acid medium, that is to say, for example with olefins, such as propylene, or alcohols, such as ethanol.

The (mono- or di-)imino-lower alkyl esters are obtained, for example, by acid-catalysed addition of alcohols to the (mono-or di-)nitriles of formula II. This addition can also be catalysed by bases, for example alcoholates, such as sodium methoxide. The (mono- or di-)amides are obtained from the (mono- or di-)imino-lower alkyl esters in the manner of a Pinner cleavage by thermal decomposition of the imino ester salts at temperatures above approximately 80° C.

On the other hand, the (mono- or di-)imino-lower alkyl esters can also be prepared, for example, from (mono- or di-)carbamoyl compounds of formula II by reaction with tri-lower alkyloxonium tetrafluoroborate, especially $^\ominus$O(C$_2$H$_5$)$_3$ BF$_4^\oplus$ ("Meerwein salt").

The (mono- or di-)imino-lower alkylthiol esters are prepared, for example, by S-alkylation of the corresponding (mono- or di-)thiocarbamoyl compounds (see below); for the alkylation, for example lower alkyl halides or lower alkyl p-toluenesulfonates, can be used.

In the preparation of (mono- or di-)thiocarbamoyl compounds of formula I (Y   S and/or Z   S)

the groups $W_1$ and/or $W_2$ in a compound of formula II may be, for example: carbamoyl, lower alkyl- or di-lower alkyl-carbamoyl (in such cases, the compound of formula II corresponds to a compound of formula I), cyano or halocarbonyl. The formation of unsubstituted or mono- or di-substituted (mono- or di-)thiocarbamoyl compounds of formula I by reaction of corresponding intermediates of formula II wherein $W_1$ and/or $W_2$ are/is, for example, as defined above, with agents that introduce sulfur is known per se [see, for example, Chem. Reviews 61. 45-86 (1961)]. Intermediates of formula II wherein $W_1$ and/or $W_2$ are/is carbamoyl, lower alkyl- or di-lower alkyl-carbamoyl can be converted into unsubstituted or mono- or di-substituted (mono- or di-)thiocarbamoyl compounds of formula I, for example, by reaction with phosphorus pentasulfide (P$_4$S$_{10}$) or aluminium trisulfide (Al$_2$S$_3$) or especially with Lawesson's reagent [2,4-bis-(4-methoxyphenyl)-2,4-dithioxo-1,3,2,4-dithiadiphosphetane]. Intermediates of formula II wherein W$_1$ and/or W$_2$ are/is cyano can be converted, for example, by reaction with ammonia and hydrogen sulfide, and those wherein W$_1$ and/or W$_2$ are/is halocarbonyl, for example, by reaction with phosphorus pentachloride, hydrogen sulfide and ammonia, into (mono- or di-)thiocarbamoyl compounds of formula I.

Compounds of formula II wherein W$_1$ and W$_2$ are carboxy are prepared, for example, by oxidising a compound of formula III

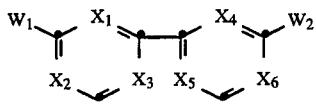 (II)

for example with KMnO$_4$ or K$_2$Cr$_2$O$_7$.

In addition, it is also possible to prepare from compounds of formula III, for example compounds of formula II wherein W$_1$ and W$_2$ are cyano by nitrosating the former, for example analogously to Chem. Pharm. Bull. 25, 1821 (1977)

[ C.A. 88, 121089 m (1978)], with ethyl nitrite in the presence of alkali metal amides in liquid ammonia to form the corresponding dialdoximes and heating these together with POCl$_3$.

Compounds of formula II wherein W$_1$ and W$_2$ are cyano are also prepared, for example, by reacting a compound of formula IV

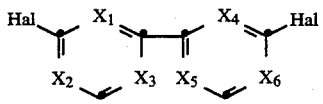 (IV)

wherein Hal is halogen, with agents introducing cyano groups, for example sodium cyanide or potassium cyanide, optionally using Pd[P(C$_6$H$_5$)$_3$]$_4$ catalysis or phase transfer catalysis, for example using 18-crown-6-ether, or with copper(I) cyanide especially in pyridine or dimethylformamide [see Chem. Rev. 87. 779 (1987)].

On the other hand, the halogen groups in a compound of formula IV can also be converted, for example by reaction with trimethylamine, into trimethylammonium halide radicals. The latter can then be converted, for example by treatment with sodium cyanide in aqueous medium, into cyano groups, compounds of formula II wherein W$_1$ and W$_2$ are cyano again being obtained.

Furthermore, it is also possible to prepare from compounds of formula IV, for example compounds of formula II wherein W$_1$ and W$_2$ are carboxy by dimetallating the former and then reacting them, for example, with CO$_2$. The metallation can be effected, for example, with agents that introduce lithium, for example n-butyllithium, to give di-(Li) intermediates. If metallation is effected with agents that introduce lithium and with copper(I) salts, then dicuprates, for example di-(CuLi), are obtained as intermediates. The metallation can also be effected, for example, with magnesium, in which case dimagnesium halides, di-(MgHal), are obtained as intermediates.

Compounds of formula II wherein W$_1$ and W$_1$ are cyano, can also be prepared for example, by diazotising a compound of formula V

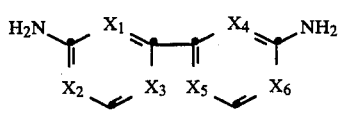 (V)

twice for example with sodium nitrite, and then reacting with, for example, copper(I) cyanide (Sandmeyer reaction).

Compounds of formula II wherein W$_1$ and W$_2$ are cyano are also prepared, for example, by oxidising a compound of formula VI

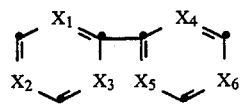 (VI)

wherein at least one of the radicals X$_2$ and X$_2$ and at least one of the radicals X$_4$ and X$_6$ is N, to a di-N-oxide, for example using meta-chloroperbenzoic acid or H$_2$O$_2$, dimethylating the di-N-oxide, for example using dimethyl sulfate, and reacting the resulting N,N'-dimethoxy derivative with, for example, sodium cyanide. Instead of dimethylating the mentioned di-N-oxide and reacting it with, for example, NaCN, it can, for example, be reacted directly with trimethylsilyl cyanide (see Synthesis 1984, 681).

Compounds of formula II wherein W$_1$ and W$_2$ are cyano, and compounds of formulae III, IV and VI, are prepared, for example, by reacting a compound of formula VIIa

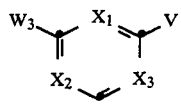 (VIIa)

with a compound of formula VIIb

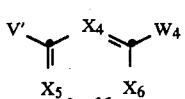 (VIIb)

In the compounds of formulae VIIa and VIIb, W$_3$ and W$_4$ are each cyano or methyl, halogen or hydrogen and V and V' are functional groups suitable for linking (hetero-)aryls to form bi-(hetero-)aryls. Suitable groups V and V' are, for example, (a) magnesium halide -MgHal and Hal (Hal   halogen)

(b) lithium -Li and Hal or (c) cuprates, for example -CuLi and Hal. Also to be mentioned is (d) the coupling of two (identical or different) lithium derivatives (V   V'   Li)

the presence of, for example, CuCl$_2$/O$_2$ or [CuI·P(n-C$_4$H$_9$)$_3$]$_4$/O$_2$ [see J. Organomet. Chem. 56, 53 (1973)]. p A further possibility consists (e) in the coupling of a compound of formula VIIa wherein V Li 

with a (N-heterocyclic) compound of formula VIIb wherein

V' H, 

see Chem. Ber. 113. 2739 (1980).

Compounds of formula V can be prepared, for example, by reducing the corresponding dinitro compounds, for example by hydrogenation or using Sn(II)Cl$_2$. Compounds of formula V can also be prepared, for example, from the corresponding compounds of formula IV by reacting the latter with an alkali metal amide, for example sodium or potassium amide.

The compounds of formula II can also be prepared by total synthesis in which case a monocyclic derivative is normally used as starting material and the second, preferably N-heterocyclic, ring is synthesised. For example, a compound of formula II wherein W$_1$ and W$_2$ are cyano, X$_1$, X$_2$, X$_3$ and X$_4$ are CH and X$_5$ and X$_6$ are N

[ 4-cyano-6-(3-cyanophenyl)-pyrimidine] 

can be obtained by way of the following synthesis steps:
(a) 3-cyanobenzoic acid chloride+malonic acid monoethyl ester→ 3-cyanophenyl-3-onepropionic acid ethyl ester
(b) product of (a)+thiourea/desulfurisation using Raney nickel →4-hydroxy-6-(3-cyanophenyl)-pyrimidine
(c, d) product of (b)+POCl$_3$, then+Cu(I)CN→4-cyano-6-(3-cyanophenyl)-pyrimidine ( desired compound of formula II).

Free compounds of formula I having salt-forming properties that are obtainable by the process of the invention can be converted into their salts in a manner known per se: compounds having basic properties by treatment with acids or suitable derivatives thereof, and compounds having acid properties by treatment with bases or suitable derivatives thereof.

Mixtures of isomers that are obtainable according to the invention can be separated into the individual isomers in a manner known per se; racemates for example, by forming salts with optically pure salt-forming reagents and separating the diastereoisomeric mixture obtainable in that manner, for example by means of fractional crystallisation.

The reactions mentioned above can be carried out under reaction conditions that are known per se, in the absence or, usually, in the presence of solvents or diluents, preferably those that are inert towards the reactants used and are solvents thereof, in the absence or presence of catalysts, condensing agents or neutralising agents, and, depending on the nature of the reaction and/or of the reactants, at reduced, normal or elevated temperature, for example in a temperature range of from approximately −70° C. to approximately 190° C., preferably from approximately −20° C. to approximately 150° C., for example at the boiling point of the solvent used, under atmospheric pressure or in a closed vessel, optionally under pressure, and/or in an inert atmosphere, for example under a nitrogen atmosphere.

The starting materials used in the process of the present invention are preferably those that result in the compounds described at the beginning as being especially valuable.

The invention also relates to those forms of the process in which a compound obtainable as intermediate at any stage of the process is used as starting material and the remaining process steps are carried out, or in which a starting material is formed under the reaction conditions or is used in the form of a derivative, for example a salt thereof.

The present invention also relates to pharmaceutical preparations that contain one of the pharmacologically active compounds of formula I as active ingredient. Preparations for enteral, especially oral, administration and also parenteral administration are especially preferred. The preparations contain the active ingredient on its own or, preferably, together with a pharmaceutically acceptable carrier. The dosage of active ingredient depends on the disease to be treated and on the species, its age, weight and individual condition, and also on the mode of administration.

The pharmaceutical preparations contain from approximately 5% to approximately 95% active ingredient, forms of administration that are in single dose form preferably containing from approximately 20% to approximately 90% active ingredient, and forms of administration that are not in single dose form preferably containing from approximately 5% to approximately 20% active ingredient. Dosage unit forms, such as dragees, tablets or capsules, contain from approximately 0.05 g to approximately 1.0 g of active ingredient.

The pharmaceutical preparations of the present invention are prepared in a manner known per se, for example by means of conventional mixing, granulating, confectioning, dissolving or lyophilising processes. For example, pharmaceutical preparations for oral administration can be obtained by combining the active ingredient with one or more solid carriers, if desired granulating a resulting mixture and, if desired, processing the mixture or granulate, if required by the addition of additional adjuvants, into tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional adjuvants are especially flowregulating agents and lubricants, for example silicic acid, talc, stearic acid or salts thereof, such as magnesium or calcium stearate, and/or polyethylene glycol, or derivatives thereof.

Dragée cores can be provided with suitable coatings which may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures, or, for the preparation of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical compositions are dry-filled capsules consisting of gelatin, and also soft sealed capsules consisting of gelatin and a plasticiser, such as glycerol or sorbitol. The dryfiller capsules may contain the active ingredient in the form of a granulate, for example in admixture with fillers, such as corn starch, binders and/or glidants, such as talc or magnesium stearate, and, if desired, stabilisers. In soft capsules, the active ingredient is preferably dissolved or suspended in suitable liquid adjuvants, such as fatty oils, paraffin oil or liquid polyethylene glycols, it likewise being possible to add stabilisers.

Other oral forms of administration are, for example, syrups prepared in customary manner which contain the active ingredient, for example, in suspended form and in a concentration of approximately from 5% to 20%, preferably approximately 10%, or in a similar concentration that provides a suitable single dose when administered, for example, in measures of 5 or 10 ml. Also suitable are, for example, powdered or liquid concentrates for preparing shakes, for example in milk. Such concentrates may also be packed in single dose quantities.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols.

For parenteral administration there are suitable, especially, aqueous solutions of an active ingredient in water-soluble form, for example in the form of a water-soluble salt, or aqueous injection suspensions that contain viscosity-increasing substances, for example sodium carboxymethylcellulose, sorbitol and/or dextran and, if desired, stabilisers. The active ingredient, optionally together with adjuvants, can also be in the form of a lyophilisate and can be made into a solution prior to parenteral administration by the addition of suitable solvents.

The solutions used, for example, for parenteral administration can also be used as infusion solutions.

The invention relates also to a method of treating the pathological conditions mentioned above. The compounds of the present invention can be administered prophylactically or therapeutically, and are preferably administered in the form of pharmaceutical preparations. A daily dose of from approximately 0.1 g to approximately 10 g, preferably from approximately 0.5 g to approximately 5 g, of a compound of the present invention will le administered in the case of a body weight of approximately 70 kg.

The following Examples illustrate the present invention; temperatures are given in degrees Celsius.

EXAMPLE 1: 2,2'-diamidino-4,4'-bipyridine dihydrochloride 0.028 g (0.0012 g-atom) of sodium is dissolved under nitrogen in 15 ml of absolute methanol. 2.5 g (0.0124 mol) of 2,2'-dicyano-4,4'-bipyridine [Experientia 30. 843 (1974)] are added to this solution and the resulting mixture is stirred for 2 days at room temperature. After the addition of 1.53 g (0.0286 mol) of ammonium chloride, 10 ml of absolute methanol and 20 ml of saturated ethanolic ammonia solution, the reaction mixture is heated for 1 hour at approximately 70° and then left to stand overnight at room temperature. The suspension is concentrated by evaporation, dissolved in water and washed with methylene chloride. The aqueous phase is concentrated to dryness by evaporation and the residue is recrystallised twice from dilute hydrochloric acid. The monohydrate of the title compound is obtained, m.p. >280°.

EXAMPLE 2: 6,6'-diamidino-2,2'-bipyridine dihydrochloride

Starting from 15 g of 6,6'-dicyano-2,2'-bipyridine, the title compound, m.p. >300°, is prepared analogously to Example 1.

The starting compounds are prepared as follows:
(a) 6,6'-dicyano-2,2'-bipyridine 11.1 f (0.06 mol) of 2,2'-bipyridine di-N-oxide [J. Heterocycl. Chem.11, 299 (1974)] are added to 11.4 ml (0.12 mol) of dimethyl sulfate at 75°. A thick suspension is formed to which a further 11.4 ml (0.12 mol) of dimethyl sulfate are added. The mixture is then heated at 80° for a further 15 minutes, cooled and concentrated by evaporation under a high vacuum. The residue is dissolved in 30 ml of water and slowly added dropwise to an ice-cooled solution of 17.4 g (0.33 mol) of sodium cyanide in 66 ml of water. The 6,6'-dicyano-2,2'-bipyridine crystallises out during the addition of the sodium cyanide. When the addition is complete, the mixture is diluted with 60 ml of water, filtered and washed with water and the product is dried under a high vacuum. The crude product is stirred with a small amount of ethanol, filtered off and dried again; m.p. 255°–258°.

EXAMPLE 3: 2,2'-dicarbamoyl-4,4'-bipyridine dihydrochloride 5.5 g (0.025 mol) of 2,2'-dicyano-4,4'-bipyridine are dissolved in 300 ml of chloroform and 32.5 ml (0.56 mol) of absolute ethanol and the solution is saturated with dry hydrogen chloride gas at room temperature. The reaction mixture is then stirred at room temperature for 24 hours. The suspension is filtered and the solid material is dried under a high vacuum to give the title compound, m.p. 280° (decomposition).

EXAMPLE 4: 4,4'-diamidino-2,2'-bipyridine dihydrochloride 0.5 m of 1.1N sodium methoxide in absolute methanol is added to a suspension of 1.2 g (0.0058 mol) of 4,4'-dicyano-2,2'-bipyridine in 48 ml of absolute methanol and the whole is boiled for 5 hours under reflux. 0.05 M of glacial acetic acid, 0.72 g (0.0134 mol) of ammonium chloride and 10 ml of 4.6N methanolic ammonia solution are then added to the solution while it is still warm and the whole is boiled for a further one hour. The cooled reaction mixture is concentrated by evaporation, taken up in 60 ml of 0.1N hydrochloric acid, filtered and applied to a column of 250 ml of Amberlite ® ER 180 adsorber resin. Washing is effected with distilled water and 5 ml fractions are collected. Fractions 14–21 are combined and concentrated by evaporation and the residue is crystallised from a small amount of water to give the title compound; m.p. >280°.

The starting compound is prepared as follows:

A suspension of 4.73 g (0.0195 mol) of 4,4'-dicarbamoyl-2,2'-bipyridine [J. Am. Chem. Soc. 80. 2745 (1958)]

and 5.67 g (0.0476 mol) of thionyl chloride in 30 ml of pyridine is stirred for 16 hours at 100°. After cooling, the reaction mixture is diluted with 100 ml of methylene chloride, filtered and concentrated to dryness by evaporation. The residue is then chromatographed with methylene chloride over silica gel. In this manner, 4,4'-dicyano-2,2'-bipyridine is obtained in the form of white crystals having a melting point of 238°–240°.

EXAMPLE 5: 3,3'-diamidino-biphenyl dihydrochloride 1.0 g (3.6 mmol) of 3,3'-dithiocarbamoyl-biphenyl (see Example 14) are suspended under nitrogen in 45 ml of dry methylene chloride, and 1.4 g (7.3 mmol) of triethyloxonium tetrafluoroborate are added at room temperature. After 2 hours, a mixture of 348 mg (2.5 mmol) of potassium carbonate and 0.35 ml of water is added to the reaction solution, stirred briefly and filtered and the filtrate is washed with ice-water. The organic phase is dried over sodium sulfate and concentrated by evaporation. the crude di-thioimino ether, 530 mg (1.6 mmol), is dissolved in 5 ml of absolute ethanol; 0.203 g (3.8 mmol) of ammonium chloride is added and the whole is heated under reflux for 6 hours. After cooling, filtration is carried out, a small amount of ethanolic hydrochloric acid is added to the filtrate and the whole is concentrated by evaporation. The title compound is purified by chromatography on Amberlite® XAD 1180 (water as eluant); m.p. 230°–235°.

EXAMPLE 6: 2-amidino-6-(3-amidinophenyl)-pyridine

Starting from 2.0 g of 2-cyano-6-(3-cyanophenyl)-pyridine, the title compound is prepared analogously to Example 1.

The starting compounds are prepared as follows:
(a) 2-(3-cyanophenyl)-pyridine N-oxide
Starting from 2-(3-cyanophenyl)-pyridine, the title compound is prepared by oxidation with $H_2O_2$ in glacial acetic acid [J. Heterocycl. Chem. 11. 299 (974)].
(b) 2.cyano-6-(3-cyanophenyl)-pyridine
Starting from 2-(3-cyanophenyl)-pyridine N-oxide, the title compound is prepared analogously to Example 2a.

EXAMPLE 7: 4-amidino-2-(3-amidinophenyl)-pyridine

Starting from 2.0 g of 4-cyano-2-(3-cyanophenyl)-pyridine, the title compound is prepared analogously to Example 1.

The starting compounds are prepared as follows:
(a) 4-chloro-2-(3-bromophenyl)-pyridine
Starting from 3-bromophenyllithium, 4-chloropyridine and chloroformic acid phenyl ester (for the acylation of the pyridine nitrogen), the title compound is prepared analogously to J. Org. Chem. 50, 4410 (1985). A corresponding 1-acyl-1,2-dihydropyridine is formed as intermediate and is aromatised by reaction with o-chloroanil ( 3,4,5,6-tetrachloro-1,2-benzoquinone)

to form the title compound.
(b) 4-cyano-2-(3-cyanophenyl)-pyridine
Starting from 4-chloro-2-(3-bromophenyl)-pyridine, the title compound is prepared by reaction with copper cyanide in boiling N,N-dimethylformamide.

EXAMPLE 8: 2-amidino-4-(3-amidinophenyl)-pyridine

Starting from 2-cyano-4-(3-cyanophenyl)-pyridine, the title compound is prepared analogously to Example 1.

The starting compounds are prepared as follows:
(a) 4.(3-cyanophenyl)-pyridine N-oxide
Starting from 4-(3-cyanophenyl)-pyridine, the title compound is prepared by oxidation with $H_2O_2$ in glacial acetic acid [J. Heterocycl. Chem. 11, 299 (1974)].
(b) 2.cyano-4-(3-cyanophenyl)-pyridine
Starting from 4-(3-canophenyl)-pyridine N-oxide, the title compound is prepared analogously to Example 2a.

EXAMPLE 9: 4-amidino-6-(3-amidinophenyl)-pyrimidine

Starting from 4-cyano-6-(3-cyanophenyl)-pyrimidine, the title compound is prepared according to the Pinner method for orthoester and amidine synthesis (for example, 1. reaction with HCl gas and absolute ethanol in methylene chloride; 2. reaction with ammonia).

The starting compounds are prepared as follows:
(a) 6-(3-cyanophenyl)-4-hydroxypyrimidine
Starting from 6-(3-cyanophenyl)-4-hydroxy-2-methylthiopyrimidine

[ 4-(3-cyanophenyl)-6-hydroxy-2-methylthiopyrimidine, see Example 10 a], the title compound is obtained by desulfurisation with Raney nickel in boiling ethanol.
(b) 4-chloro-6-(3-cyanophenyl)-pyrimidine
6-(3-cyanophenyl)-4-hydroxypyrimidine is boiled under reflux with phosphorus oxychloride to give the title compound.
(c) 4-cyano-6-(3-cyanophenyl)-pyrimidine
4-chloro-6-(3-cyanophenyl)-pyrimidine is reacted with copper cyanide in boiling N,N-dimethylformamide to give the title compound.

EXAMPLE 10: 2-amidino-4-(3-amidinophenyl)-pyrimidine

Starting from 2-cyano-4-(3-cyanophenyl)-pyrimidine, the title compound is prepared according to the Pinner method for orthoester and amidine synthesis (for example, 1. reaction with HCl gas and absolute ethanol in methylene chloride; 2. reaction with ammonia).

The starting compounds are prepared as follows:
(a) 4-(3-cyanophenyl)-6-hydroxy-2-metbylthiopyrimidine
4.3 g (0.02 mol) of 3-(3-cyanophenyl)-3-oxopropionic acid ethyl ester and 2.2 g (0.02 mol) of S-methylisothiuronium iodide are added to a solution of 1.1 g (0.02 mol) of potassium hydroxide in 5 ml of distilled water and the whole is stirred for 16 hours at room temperature. The reaction mixture is filtered and the filtrate is adjusted to pH 4 using glacial acetic acid. The product which crystallises out is filtered off with suction, dried and recrystallised from methanol to give the title compound; m.p. >220°.
(b) 4.(3-cyanophenyl)-6-chloro-2-methylthiopyrimidine
A suspension of 4-(3-cyanophenyl)-6-hydroxy-2-methylthiopyrimidine in phosphorus oxychloride is stirred for 5 hours at 110°. The reaction mixture is concentrated by evaporation, ice-water is added and the whole is adjusted to pH 5–6 by the addition of 10N sodium hydroxide solution. The undissolved material is filtered off with suction, washed with water and dried in vacuo to give the title compound. [Analogously to J. pharm. Soc. Japan 70, 137 (1950)].

(c) 4.(3-cyanophenyl)-2-methylthiopyrimidine

Starting from 4-(3-cyanophenyl)-6-chloro-2-methylthiopyrimidine, the title compound is obtained analogously to J. pharm. Soc. Japan 70, 137 (1950) by reduction with zinc in the presence of 5% aqueous ammonia.

(d) 4-(3-cyanophenyl)-2-methylsulfonylpyrimidine 4-(3-cyanophenyl)-2-methylthiopyrimidine is suspended in distilled water and reacted to form the title compound analogously to Recl. Trav. Chim. (Pays-Bas) 93, 325 (1974) by passing chlorine through.

(e) 2-cyano-4-(3-cyanophenyl)-pyrimidine

A mixture of 4-(3-cyanophenyl)-2-methylsulfonylpyrimidine and potassium cyanide in N,N-dimethylformamide is stirred for 4 hours at 100°. The reaction mixture is concentrated by evaporation, distilled water is added thereto and the whole is extracted with methylene chloride. The organic phase is dried and concentrated by evaporation to give the title compound.

EXAMPLE 11: 4,4'-dithiocarbamoyl-2,2'-bipyridine

A solution of 2 g (0.01 mol) of 4,4'-dicyano-2,2'-bipyridine and 2.74 ml (0.02 mol) of triethylamine in 50 ml of pyridine is saturated with hydrogen sulfide, stirred for 5 hours at 40° and finally for 16 hours at room temperature. The reaction mixture is poured onto water and the precipitated product is filtered off with suction, washed with water and dried to give the title compound.

EXAMPLE 12: 6,6'-dithiocarbamoyl-2,2'-bipyridine

Starting from 6,6'-dicyano-2,2'-bipyridine, the title compound is prepared analogously to Example 11.

EXAMPLE 13

The following compounds are prepared analogously to Examples 1 to 3:
(a) 3,3'-dicarbamoyl-biphenyl, m.p. 293°–295°
(b) 4-amidino-2-(3-amidinophenyl)-pyrimidine
(c) 4-amidino-2-(6-amidinopyrid-2-yl)-pyrimidine
(d) 2-amidino-4-(6-amidinopyrid-2-yl)-pyrimidine
(e) 6,6'-dicarbamoyl-2,2'-bipyridine
(f) 6,6'-bis-N-methylamidino-2,2'-bipyridine dihydrochloride, m.p. >300°, IR (KBr): 1670, 1621, 1563, 1420, 976, 800, 685 cm$^{-1}$
(g) 6,6'-bis-1-piperidinoiminomethyl-2,2'-bipyridine
(h) 6,6'-bis-1-pyrrolidinoiminomethyl-2,2'-bipyridine dihydrochloride, m.p >300°, IR (KBr): 1666, 1620, 1570, 1423, 990, 814 cm$^{-1}$
(i) 6,6'-bis-N-hydroxyamidino-2,2'-bipyridine dihydrochloride, m.p. 280°–284°
(j) 6,6'-bis-N-aminoamidino-2,2'-bipyridine
(k) 6,6'-bis-N-cyclopentylamidino-2,2'-bipyridine dihydrochloride, m.p. >300°, IR (KBr): 1669, 1630, 1442, 991, 753 cm$^{-1}$
(l) 6,6'-bis-N,N-dimethylamidino-2,2'-bipyridine dihydrochloride, m.p. 310–°312°, IR (KBr): 1674, 1580, 1428, 994, 821 cm$^{-1}$ EXAMPLE 14: 3,3'-dithiocarbamoyl-biphenyl 1.0 g (4.9 mmol) of 3,3'-dicyano-biphenyl is dissolved in 22 ml of pyridine and 1.4 ml (9.8 mmol) of triethylamine. Dry hydrogen sulfide is introduced into the yellow solution for 7 hours at 40°. The green reaction solution is stirred for a further 15 hours at 40°, cooled and poured into water. The mixture is extracted with methylene chloride, the organic phase is dried with sodium sulfate, concentrated by evaporation and the title compound is recrystallised from a small amount of methylene chloride; m.p. 188°–190°.

EXAMPLE 15:
4,4'-bis-N-n-propylcarbamoyl-2,2'-bipyridine 0.535 g (21 mmol) of 2-ethyl-5-phenylisoxazolium 3'-sulfonate (Woodward's reagent K, Fluka) is added with stirring to a solution of 0.258 g (10.5 mmol) of 2,2'-bipyridine-4,4'-dicarboxylic acid in 10 ml of dimethylformamide and 0.29 ml of triethylamine. Stirring is continued until the first-mentioned reagent has completely dissolved (approximately 1 hour) and then 0.18 ml of n-propylamine is added to the yellow solution. The reaction mixture is stirred for a further 5 hours at room temperature and the precipitated product is filtered off with suction and recrystallised from ethanol to give the title compound in the form of white crystals; m.p. 290°–291°.

EXAMPLE 16: Capsules each containing 0.25 g of active ingredient, for example one of the compounds of Examples 1–15, can be prepared as follows:

Composition (for 5000 capsules)

active ingredient 1250 g
talc 180 g
wheat starch 120 g
magnesium stearate 80 g
lactose 20 g The pulverulent substances are forced through a sieve having a mesh size of 0.6 mm and mixed. 0.33 g portions of the mixture are introduced into gelatin capsules by means of a capsule-filling machine.

What is claimed is:

1. A compound of formula I

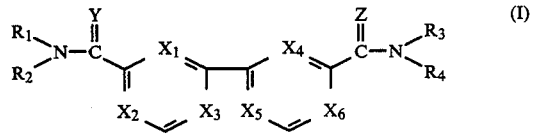

wherein one of $X_1$, $X_2$ and $X_3$ is N, and the other two of $X_1$, $X_2$ and $X_3$ are CH; one of $X_4$, $X_5$ and $X_6$ is N, and the other two of $X_4$, $X_5$ and $X_6$ are CH; Y is $NR_5$, O or S, Z is $NR_6$, O or S each of the radicals $R_2$, $R_4$, $R_5$ and $R_6$, independently of the others, is hydrogen or lower alkyl and each of the radicals $R_1$ and $R_3$ independently of the other, is hydrogen, lower alkyl $C_3$–$C_8$ cycloalkyl, phenyl-lower alkyl phenyl, naphthyl carboxy, lower alkoxycarbonyl, carbamoyl, N-lower alkylcarbamoyl, N,N-di-lower alkylcarbamoyl, cyano, hydroxy, lower alkoxy, lower alkanoyloxy amino, lower alkylamino, and di-lower alkyl amino with the proviso that Y is $NR_5$ or S and Z is $NR_6$ or S when $X_3$ and $X_5$ are N and $X_1$, $X_2$, $X_4$ and $X_6$ are CH; a tautomer thereof, or a salt thereof.

2. A compound of formula I according to claim 1, wherein Y is NH, O or S, Z is NH, O or S, each of the radicals $R_2$ and $R_4$, independently of the other, is hydrogen or lower alkyl and each of the radicals $R_1$ and $R_3$, independently of the other, is hydrogen, lower alkyl, $C_3$–$C_8$cycloalkyl, phenyl-lower alkyl, phenyl, carboxy, hydroxy or amino; with the proviso that Y and Z are NH or S when $X_3$ and $X_5$ are N and $X_1$, $X_2$, $X_4$ and $X_6$ are CH; a tautomer thereof, or a salt thereof.

3. A compound of formula I according to claim 1, wherein Y is NH, Z is NH, each of the radicals $R_2$ and $R_4$, independently of the other, is hydrogen or lower alkyl and each of the radicals $R_1$ and $R_3$, independently of the other, is hydrogen, lower alkyl, $C_3$–$C_8$cycloalkyl, phenyl-lower alkyl, phenyl, carboxy, hydroxy or amino; a tautomer thereof, or a salt thereof.

4. A compound of formula I according to claim 1, wherein (a) $X_1$ and $X_4$ are N and $X_2$, $X_3$, $X_5$ and $X_6$ are CH or (b) $X_2$ and $X_6$ are N and $X_1$, $X_3$, $X_4$ and $X_5$ are CH; Y is NH or O, Z is NH or O, the radicals $R_2$ and $R_4$ are hydrogen and the radicals $R_1$ and $R_3$ are hydrogen, lower alkyl, hydroxy or amino, a tautomer thereof, or a pharmaceutically acceptable salt thereof.

5. A compound of formula I according to claim 1, wherein (a) $X_1$ and $X_4$ are N and $X_2$, $X_3$, $X_5$ and $X_6$ are CH or (b) $X_2$ and $X_6$ are N and $X_1$, $X_3$, $X_4$ and $X_5$ are CH; Y is NH, Z is NH, the radicals $R_2$ and $R_4$ are hydrogen and the radicals $R_1$ and $R_3$ are hydrogen, lower alkyl, $C_5$–$C_6$cycloalkyl or hydroxy, a tautomer thereof, or a pharmaceutically acceptable salt thereof.

6. A compound of formula I according to claim 4, wherein $R_1$, $R_2$, $R_3$ and $R_4$ are hydrogen.

7. A compound of formula I according to claim 5, wherein $R_1$, $R_2$, $R_3$ and $R_4$ are hydrogen.

8. 2,2'-diamidino-4,4'-bipyridine or a pharmaceutically acceptable salt thereof according to claim 5.

9. 6,6'-diamidino-2,2'-bipyridine or a pharmaceutically acceptable salt thereof according to claim 5.

10. 6,6'-bis-N-methylamidino-2,2'-bipyridine or a pharmaceutically acceptable salt thereof according to claim 5.

11. 6,6'-bis-N-hydroxyamidino-2,2'-bipyridine or a pharmaceutically acceptable salt thereof according to claim 5.

12. A pharmaceutical composition comprising a therapeutically effective amount of a compound according to claim 1 and at least one pharmaceutically acceptable carrier material.

13. A pharmaceutical composition according to claim 12 comprising a therapeutically effective amount of 6,6'-diamidino-2,2'-bipyridine, or a pharmaceutically acceptable salt thereof.

* * * * *